(12) United States Patent
O'Connell et al.

(10) Patent No.: US 6,730,797 B2
(45) Date of Patent: May 4, 2004

(54) PROCESS FOR PRODUCING CRYSTALLINE ATORVASTATIN CALCIUM

(75) Inventors: John O'Connell, Rochestown (IE); William Tully, Midleton (IE); Evelyn Madigan, Carrigaline (IE)

(73) Assignee: Pfizer Science and Technology Ireland Limited, Dublin (IE)

( * ) Notice: Subject to any disclaimer, the term of this patent is extended or adjusted under 35 U.S.C. 154(b) by 0 days.

(21) Appl. No.: 10/637,886

(22) Filed: Aug. 8, 2003

(65) Prior Publication Data

US 2004/0024226 A1 Feb. 5, 2004

Related U.S. Application Data

(63) Continuation of application No. 10/172,614, filed on Jun. 14, 2002, now Pat. No. 6,605,728, which is a continuation of application No. PCT/IE00/00151, filed on Dec. 18, 2000.

(30) Foreign Application Priority Data

Dec. 17, 1999 (IE) .................... PCT/IE99/00133

(51) Int. Cl.[7] ......................................... C07D 207/335
(52) U.S. Cl. ....................................................... 548/537
(58) Field of Search .......................................... 548/537

(56) References Cited

U.S. PATENT DOCUMENTS

| | | |
|---|---|---|
| 3,852,480 A | 12/1974 | Williams |
| 3,897,307 A | 7/1975 | Porubcan et al. |
| 4,681,893 A | 7/1987 | Roth |
| 5,003,080 A | 3/1991 | Butler et al. |
| 5,097,045 A | 3/1992 | Butler et al. |
| 5,102,648 A | 4/1992 | Carpenter et al. |
| 5,103,024 A | 4/1992 | Millar et al. |
| 5,109,488 A | 4/1992 | Dijkstra et al. |
| 5,124,482 A | 6/1992 | Butler et al. |
| 5,149,837 A | 9/1992 | Butler et al. |
| 5,155,251 A | 10/1992 | Butler et al. |
| 5,216,174 A | 6/1993 | Butler et al. |
| 5,245,047 A | 9/1993 | Butler et al. |
| 5,248,793 A | 9/1993 | Millar et al. |
| 5,273,995 A | 12/1993 | Roth |
| 5,280,126 A | 1/1994 | Butler et al. |
| 5,298,627 A | 3/1994 | Butler et al. |
| 5,342,952 A | 8/1994 | Butler et al. |
| 5,397,792 A | 3/1995 | Butler et al. |
| 5,446,054 A | 8/1995 | Butler et al. |
| 5,470,981 A | 11/1995 | Butler et al. |
| 5,489,690 A | 2/1996 | Butler et al. |
| 5,489,691 A | 2/1996 | Butler et al. |
| 5,510,488 A | 4/1996 | Butler et al. |
| 5,969,156 A | 10/1999 | Briggs et al. |
| 5,998,633 A | 12/1999 | Jacks et al. |
| 6,087,511 A | 7/2000 | Lin et al. |
| 6,121,461 A | 9/2000 | McKenzie |

FOREIGN PATENT DOCUMENTS

| | | |
|---|---|---|
| WO | WO 97/03958 | 2/1997 |
| WO | WO 97/03959 | 2/1997 |
| WO | WO 99/32434 | 7/1999 |

OTHER PUBLICATIONS

PCT International Search Report for PCT/IE00/00150.
Brower, et al, "The Synthesis of (4R–cis)–1,1–Dimethyl-ethyl 6–cyanomethyl–2, 2–dimethyl–1, 3–dioxane–4–acetate, a Key Intermediate for the Preparation of CI–981, a Highly Potent, Tissue Selective Inhibitor of HMG–CoA Reductase", Tetrahedron Letters, vol. 33, No.17, 1992; pp. 2279–2282.
Baumann, et al, "The Convergent Synthesis of CI–981, an Optically Active, Highly Potent, Tissue Selective Inhibitor of HMG–CoA Reductase", Tetrahedron Letters, vol. 33, No. 17, 1992; pp. 2283–2284; XP 00608147.
PCT International Search Report for PCT/IE00/00151.
Graul, et al, "Atorvastatin Calcium", Drugs of the Future, ES, Barcelona, vol. 22, No. 9, 1997; pp. 956–968–968, XP000904817.

*Primary Examiner*—Joseph K. McKane
*Assistant Examiner*—Kamal Saeed
(74) *Attorney, Agent, or Firm*—Francis J. Tinney

(57) ABSTRACT

A factory scale process for producing crystalline atorvastatin calcium includes the step of drying the isolated product in a vacuum pan dryer. The vacuum pan dryer has an agitator which is continuously rotated at a speed of approximately 1 rpm. High quality material is routinely and consistently produced with reduced cycle time.

8 Claims, No Drawings

PROCESS FOR PRODUCING CRYSTALLINE ATORVASTATIN CALCIUM

RELATED APPLICATIONS

This application is a continuation application of U.S. Ser. No. 10/172,614, filed Jun. 14, 2002, now U.S. Pat. No. 6,605,728, which is a continuation of PCT/IE00/00151, filed Dec. 18, 2000, which claims benefit of PCT/IE99/00133, filed Dec. 17, 1999, all of which are incorporated herein by reference in their entirety.

FIELD OF THE INVENTION

The invention relates to an improved process for producing crystalline atorvastatin calcium which is known by the chemical name [R-(R*,R*)]-2-(4-fluorophenyl)-β,δ-dihydroxy-5-(1-methylethyl)-3-phenyl-4-[(phenylamino) carbonyl]-1H-pyrrole-1-heptanoic acid hemi calcium salt.

BACKGROUND OF THE INVENTION

Atorvastatin is useful as a selective and competitive inhibitor of the enzyme 3-hydroxy-3-methylglutaryl-coenzyme A (HMG-CoA) reductase, the rate-limiting enzyme that converts 3-hydroxy-3-methylglutaryl-coenzyme A to mevalonate, a precursor of sterols such as cholesterol. The conversion of HMG-CoA to mevalonate is an early and rate-limiting step in cholesterol biosynthesis.

Atorvastatin as well as some of its metabolites are pharmacologically active in humans and are thus useful as a hypolipidemic and hypocholesterolemic agent. The liver is the primary site of action and the principal site of cholesterol synthesis. Clinical and pathological studies show that elevated plasma levels of total cholesterol and associated triglycerides promote human atherosclerosis and are risk factors for developing cardiovascular disease.

U.S. Pat. No. 4,681,893, which is herein incorporated by reference, discloses certain trans-6-[2-(3- or 4-carboxamido-substituted-pyrrol-1-yl)alkyl]-4-hydroxy-pyran-2-ones including trans (±)-5-(4-fluorophenyl)-2-(1-methylethyl)-N,4-diphenyl-1-[(2-tetrahydro-4-hydroxy-6-oxo-2H-pyran-2yl)ethyl]-1H-pyrrole-3-carboxamide.

U.S. Pat. No. 5,273,995, which is herein incorporated by reference, discloses the enantiomer having the R form of the ring-opened acid of trans-5-(4-fluorophenyl)-2-(1-methylethyl)-N,4-diphenyl-1-[(2-tetrahydro-4-hydroxy-6-oxo-2H-pyan-2-yl)ethyl]-1H-pyrrole-3-carboxamide, i.e., [R-(R*,R*)]-2-(4-fluorophenyl)-β,δ-dihydroxy-5-(1-methylethyl)-3-enyl-4-[(phenylamino)carbonyl]-1H-pyrrole-1-heptanoic acid.

The above described atorvastatin compounds have been prepared by a superior convergent route disclosed in the following U.S. Pat. Nos. 5,003,080; 5,097,045; 5,103,024; 5,124,482; and 5,149,837, which are herein incorporated by reference and Baumann K. L., Butler D. E., Deering C. F., et al, *Tetrahedron Letters* 1992;33:2283–2284.

One of the critical intermediates disclosed in U.S. Pat. No. 5,097,045 has also been produced using novel chemistry, as disclosed in U.S. Pat. No. 5,155,251, which is herein incorporated by reference and Brower P. L., Butler D. E. Deering C. F. et al. *Tetrahedron Letters* 1992:33:2279–2282.

U.S. Pat. Nos. 5,216,174; 5,245,047; 5,248,793; 5,280,126; 5,397,792; 5,342,952; 5,298,627; 5,446,054; 5,470,981; 5,489,690; 5,489,691; 5,109,488; 5,969,156; 6,087,511; 5,998,663 and WO99/32434 which are herein incorporated by reference, disclose various processes and key intermediates for preparing atorvastatin.

It has been found that when the process for preparing atorvastatin calcium was scaled up to a commercial factory scale, drying was slow and difficult to optimize.

It was also found that wet crystalline atorvastatin calcium was susceptible to possible break up with physical attrition and furthermore had a propensity to form rock hard clods on mixing.

The object of the present invention is therefore to provide a process for producing crystalline atorvastatin calcium on a factory scale which routinely and consistently produces high quality material with reduced cycle time.

SUMMARY OF THE INVENTION

According to the invention there is provided a process for producing crystalline atorvastatin trihydrate hemi calcium salt comprising the steps of:

(a) reacting a mixture of atorvastatin lactone, methanol, and methyl tert-butyl ether with sodium hydroxide to form the ring-opened sodium salt:

(b) forming a product rich aqueous layer and an organic layer comprising methyl tert-butyl ether containing impurities;

(c) removing the organic layer comprising methyl tert-butyl ether containing impurities;

(d) extracting the product rich aqueous layer with methyl tert-butyl ether;

(e) adding an extra charge of methyl tert-butyl ether to a vessel containing the product rich aqueous layer in an amount of at least 1% w/v of the contents of the vessel;

(f) sealing the reaction vessel;

(g) heating the contents of the sealed reaction vessel to 47° C. to 57° C. in the presence of the extra charge of methyl tert-butyl ether which saturates the the crystallization matrix on heating;

(h) adding calcium acetate hemihydrate to the sealed reaction vessel to form atorvastatin trihydrate hemi calcium salt; and (i) drying the isolated product in a vacuum pan dryer having an agitator which is continuously rotated at a speed of from 0.5 to 2 rpm.

It has been surprisingly found that this continuous agitation at a very low speed provides optimum drying conditions with very significant increased throughput while avoiding clod formation and particle attrition. As more solvents are evaporated from the cake in the dryer, the crystals are increasingly susceptible to attrition. The process ensures that no break-up occurs with physical attrition. Clod formation on mixing is also avoided.

In a particularly preferred embodiment of the invention, the agitator is substantially continuously rotated at a speed of approximately 1 rpm. This provides reduced drying time while ensuring uniform drying of the crystals, avoidance of clod formation and particle attrition. We have found that this uniform drying ensures that all water is evenly removed from the cake in the dryer.

In a preferred embodiment the vacuum in the pan dryer is maintained at from −0.80 to −0.99 bar.

Preferably, the isolated product is dried over a period of from 1 to 4 days, ideally over a period of from 1 to 2 days.

DETAILED DESCRIPTION OF THE INVENTION

Atorvastatin lactone is saponified in a water/methyl alcohol/methyl tert-butyl ether (2-methoxy-2-methylpropane; tert-butyl methyl ether) mixture with sodium hydroxide. The aqueous layer containing the sodium salt of atorvastatin is washed with methyl tert-butyl ether to remove small quantities of process impurities. A small aliquot of methyl tert-butyl ether is added to the crystallization matrix. Sodium-to-calcium salt metathesis with concurrent crystallization is accomplished by the slow addition of an aqueous calcium acetate solution to the sodium salt solution. To ensure crystallization simultaneous with addition, the reaction mixture is seeded with crystalline atorvastatin shortly after the start of the calcium acetate addition. The product is isolated by filtration and, after washing with water/methyl alcohol and water, is centrifuged and vacuum dried before milling to give crystalline atorvastatin as the trihydrate. The reaction scheme is shown below.

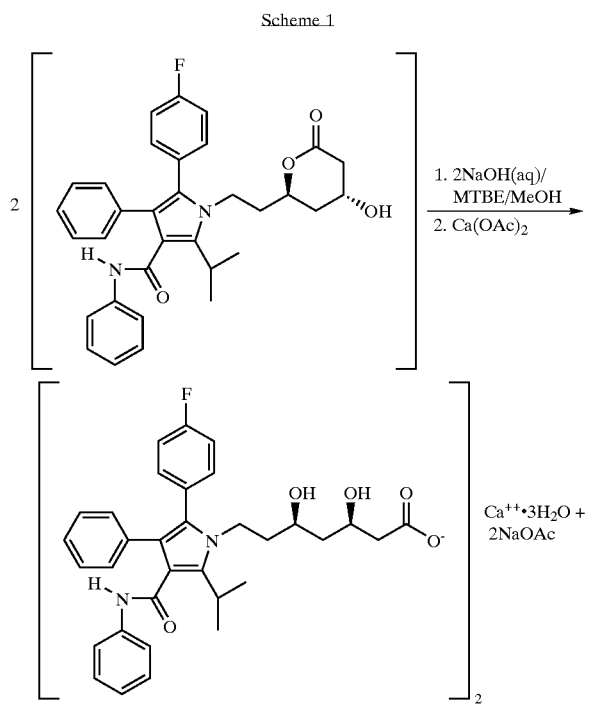

Scheme 1

We have surprisingly found that the drying of atorvastatin calcium has a sensitive window of moisture content of approximately 6% w/v where the drying has to proceed slowly in order to prevent the particles from breaking down. As more solvents are evaporated from the cake in the dryer, especially around 6% water, the particles are increasingly susceptible to attrition.

We have found that continuous agitation at approximately 1 rpm significantly reduces the drying time-compared to an intermittent agitation technique, thereby increasing drying capacity while ensuring that the final dried product is within a consistent range for particle size and bulk density. This is in complete contrast to continuous medium speed agitation which results in clod formation and the risk of physical attrition and intermittent agitation which substantially increases the required drying time. Continuous agitation at 0.5 to 2 rpm is outside the normal design operating range of agitated pan dryers.

EXAMPLE 1

250 kg atorvastatin lactone prepared as described in U.S. Pat. No. 5,273,995, the entire contents of which are incorporated by reference, 1028 kg methyl tert-butyl ether and 496 kg of methanol are charged to a 6000 L glass-lined reaction vessel. The reaction mixture is agitated and heated to about 30° C. to dissolve the lactone. When the lactone is dissolved, approximately 3200 L of caustic solution is added (19 kg of sodium hydroxide 97.5% dissolved in 3165 L deionized water). The contents of the vessel are heated to 47° C. to 57° C. and agitated for at least 45 minutes.

After cooling to 25° C. to 35° C. under an inert atmosphere, the contents are allowed to settle and the organic layer is discarded, 765 kg methyl tert-butyl ether is charged to the aqueous layer, the contents mixed and allowed to settle. The organic layer is discarded.

63 kg of extra methyl tert-butyl ether is charged to the product rich aqueous layer in the reaction vessel which is then sealed. The contents of the sealed reaction vessel are heated to 47° C. to 57° C. maintaining a pressurized system.

A solution of calcium acetate (40 kg calcium acetate hemihydrate in 1365 L deionized water) is transferred to the pressurized vessel. Shortly after commencement of the calcium acetate addition, the transfer is stopped and atorvastatin trihydrate hemi calcium salt seed, prepared as described in U.S. Pat. No. 5,969,156 which is herein incorporated by reference, is introduced.

A seed slurry is prepared by charging 37 L deionised water and 13 kg methanol to a stainless steel make-up/delivery vessel. The solvent mixture is agitated by rocking the vessel back and forth on its cradle, 3.6 kg atorvastatin calcium seed crystals are then charged to the solvent mixture. The contents of the delivery vessel are mixed by rocking until a seed slurry is formed. Sufficient pressure is applied to the make-up/delivery vessel so that its pressure is higher than that of the reaction vessel. The make-up/delivery vessel is attached to the reaction vessel via a flexible hose, and the seed slurry is charged rapidly over 2 to 3 minutes, under pressure, into the reaction vessel.

After the addition of the seed slurry, the calcium acetate addition is immediately resumed to complete the calcium transfer.

The product cake is washed first with a methanol/water solution followed by a water wash.

EXAMPLE 2

Drying of Atorvastatin Calcium

The wet product prepared in Example 1 is loaded into a stainless steel continuous agitation pan dryer such as a Guedu Pan Dryer. A full vacuum of from −0.80 to −0.99 bar is applied, the jacket of the dryer adjusted to 60° C. to 70° C. and the product dried with slow continuous agitation at approximately 1 rpm for at least 24 hours, preferably for from 1 to 4 days, ideally 1 to 2 days.

The dry product is then loaded into clean poly-lined drums.

The invention is not limited to the embodiments hereinbefore described which may be varied in detail.

What is claimed is:

1. A factory scale process for producing crystalline atorvastatin trihydrate hemi calcium salt comprising the steps of:
   (a) reacting a mixture of atorvastatin lactone, methanol, and methyl tert-butyl ether with sodium hydroxide to form the ring-opened sodium salt;
   (b) forming a product rich aqueous layer and an organic layer comprising methyl tert-butyl ether containing impurities;
   (c) removing the organic layer comprising methyl tert-butyl ether containing impurities;
   (d) extracting the product rich aqueous layer with methyl tert-butyl ether;

(e) adding an extra charge of methyl tert-butyl ether to a vessel containing the product rich aqueous layer in an amount of at least 1% w/v of the contents of the vessel;
(f) sealing the reaction vessel;
(g) heating the contents of the sealed reaction vessel to 47° C. to 57° C. in the presence of the extra charge of methyl tert-butyl ether which saturates the crystallization matrix on heating;
(h) adding calcium acetate hemihydrate to the sealed reaction vessel and shortly after commencement of the calcium acetate addition the transfer is stopped and the reaction mixture is seeded with crystalline atorvastatin calcium to form atorvastatin trihydrate hemi calcium salt;
(i) providing a vacuum pan dryer having an agitator; and
(j) drying the isolated product in a vacuum pan dryer whilst continuously rotating the agitator at a speed of from 0.5 rpm to 2 rpm.

2. The process as claimed in claim 1 comprising continuously rotating the agitator at a speed of approximately 1 rpm.

3. The process as claimed in claim 1 comprising maintaining vacuum in the pan dryer at a pressure of from −0.80 to −0.99 bar.

4. The process as claimed in claim 2 comprising maintaining vacuum in the pan dryer at a pressure of from −0.80 to −0.99 bar.

5. The process as claimed in claim 1 comprising drying the isolated product over a period of from 1 to 4 days.

6. The process as claimed in claim 2 comprising drying the isolated product over a period of from 1 to 4 days.

7. The process as claimed in claim 1 comprising drying the isolated product over a period of from 1 to 2 days.

8. The process as claimed in claim 2 comprising drying the isolated product over a period of from 1 to 2 days.

* * * * *